(12) United States Patent
Murthy et al.

(10) Patent No.: US 10,039,831 B2
(45) Date of Patent: Aug. 7, 2018

(54) POLYMER HYDROGELS FOR IN VIVO APPLICATIONS AND METHODS FOR USING AND PREPARING SAME

(75) Inventors: Niren Murthy, Atlanta, GA (US); Christopher Hermann, Atlanta, GA (US); David Scott Wilson, Atlanta, GA (US); Xinghai Ning, Atlanta, GA (US); Barbara D. Boyan, Atlanta, GA (US); Zvi Schwartz, Atlanta, GA (US); Robert Guldberg, Marietta, GA (US); Tamim Diab, Atlanta, GA (US)

(73) Assignees: Georgia Tech Research Corporation, Atlanta, GA (US); Children's Healthcare of Atlanta, Inc., Atlanta, GA (US)

(*) Notice: Subject to any disclaimer, the term of this patent is extended or adjusted under 35 U.S.C. 154(b) by 709 days.

(21) Appl. No.: 14/005,320

(22) PCT Filed: Mar. 19, 2012

(86) PCT No.: PCT/US2012/029686
§ 371 (c)(1),
(2), (4) Date: Mar. 3, 2014

(87) PCT Pub. No.: WO2012/126005
PCT Pub. Date: Sep. 20, 2012

(65) Prior Publication Data
US 2014/0171367 A1    Jun. 19, 2014

Related U.S. Application Data

(60) Provisional application No. 61/453,818, filed on Mar. 17, 2011.

(51) Int. Cl.
| | |
|---|---|
| *A61K 47/32* | (2006.01) |
| *A61K 9/06* | (2006.01) |
| *A61K 38/17* | (2006.01) |
| *C07K 14/51* | (2006.01) |
| *A61L 27/52* | (2006.01) |

(52) U.S. Cl.
CPC .............. *A61K 47/32* (2013.01); *A61K 9/06* (2013.01); *A61K 38/1709* (2013.01); *A61L 27/52* (2013.01); *C07K 14/51* (2013.01); *A61L 2430/02* (2013.01)

(58) Field of Classification Search
None
See application file for complete search history.

(56) References Cited

U.S. PATENT DOCUMENTS

2010/0130415 A1* 5/2010 Cohen .................. A61K 31/557
                                                514/8.1

FOREIGN PATENT DOCUMENTS

WO        2006109945 A     10/2006

OTHER PUBLICATIONS

Guo et al, "Surface Modification of Polymeric Micelles by Strain-Promoted Alkyne—Azide Cycloadditions," Chemistry—A European Journal, vol. 16, Issue 45, pp. 13360-13366 (Nov. 12, 2010).*
International Search Report dated Jun. 28, 2012.
The International Preliminary Report on Patentability dated Mar. 27, 2014.
Slaughter, et al., "Hydrogels in Regenerative Medicine," Advanced Materials, 2009, 21, pp. 3307-3329.
Charles, et al., Reduction of Non-Specific Protein Adsorption Using Poly(ethylene)Glycol (PEG) Modified Polyacrylate Hydrogels in Immunoassays for Staphylococcal Enterotoxin B Detection, Sensors 2009, 9, pp. 645-655.
Gibas, et al., "Review: Synthetic Polymer Hydrogels for Biomedical Applications," Chemistry & Chemical Technology, Gdansk University of Technology, Chemical Faculty, Polymer Technology Department, 80-233 Gdansk, ul Narutowicza 11/12.

* cited by examiner

*Primary Examiner* — Dennis J Parad
(74) *Attorney, Agent, or Firm* — Whitham & Cook, PC

(57) ABSTRACT

Compositions and methods are described for a polymer hydrogel created by a cycloaddition reaction between an azide and an alkyne that proceeds rapidly without catalyst to produce the polymer hydrogel in less than ninety seconds. The polymer hydrogel can be used in in vivo applications for the localized delivery of therapeutic agent in aqueous solutions. An example of therapeutic delivery of a protein in a mouse model is demonstrated.

14 Claims, 8 Drawing Sheets

Figures 3 A-D

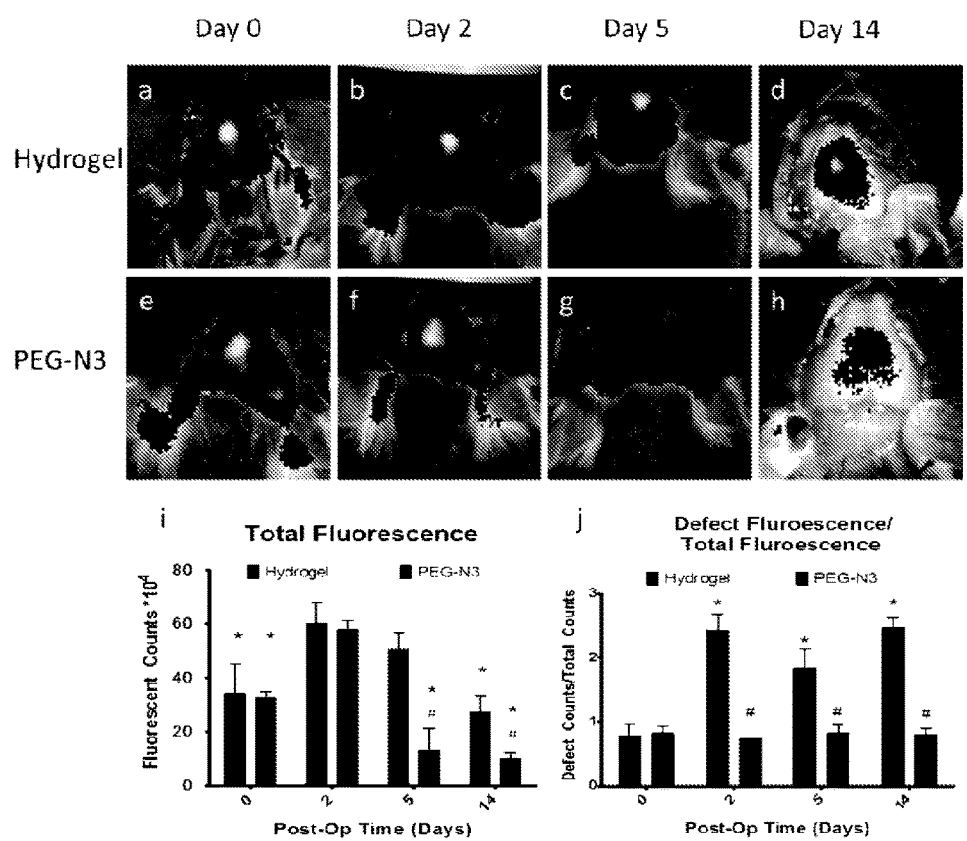
Figures 5 A-J

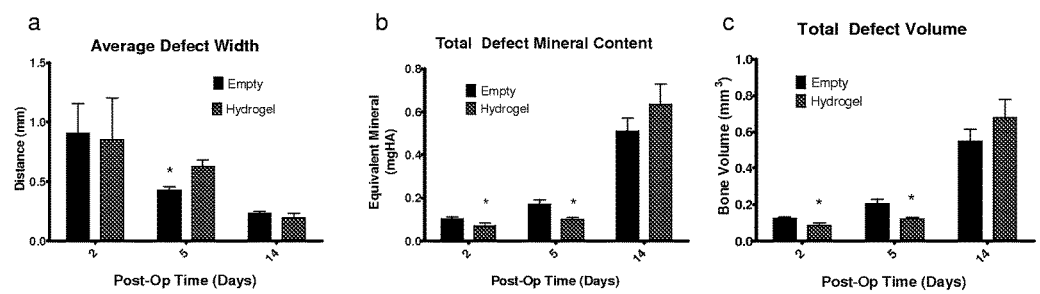
Figures 6 A-C

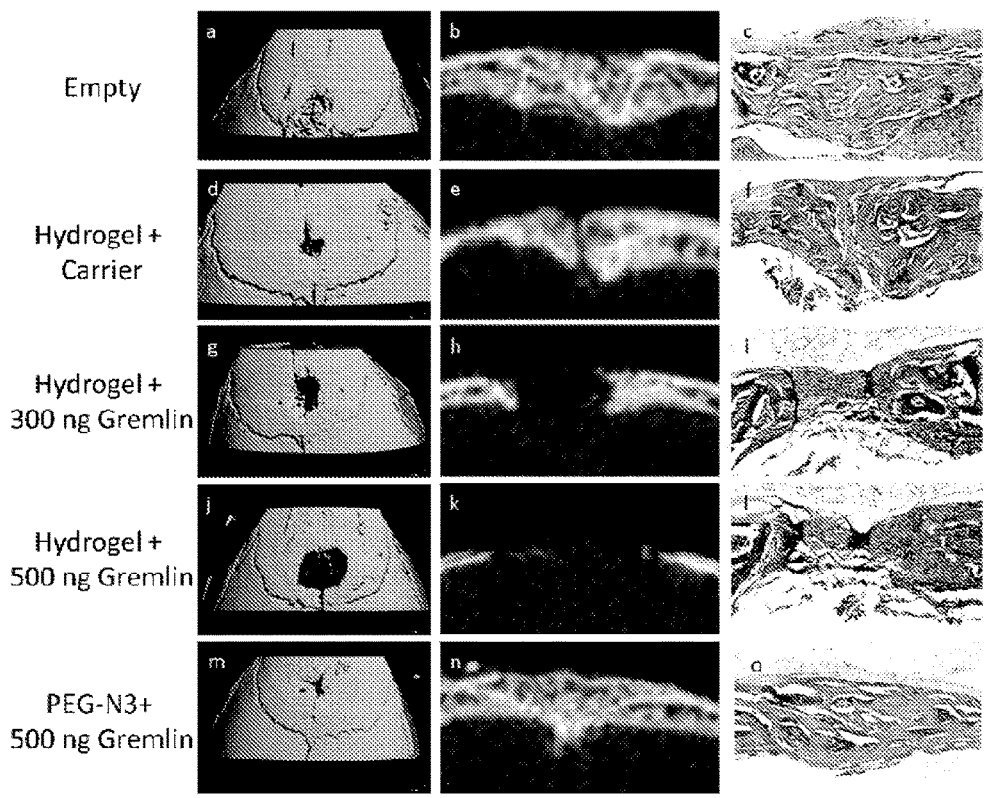
Figures 7 A-O

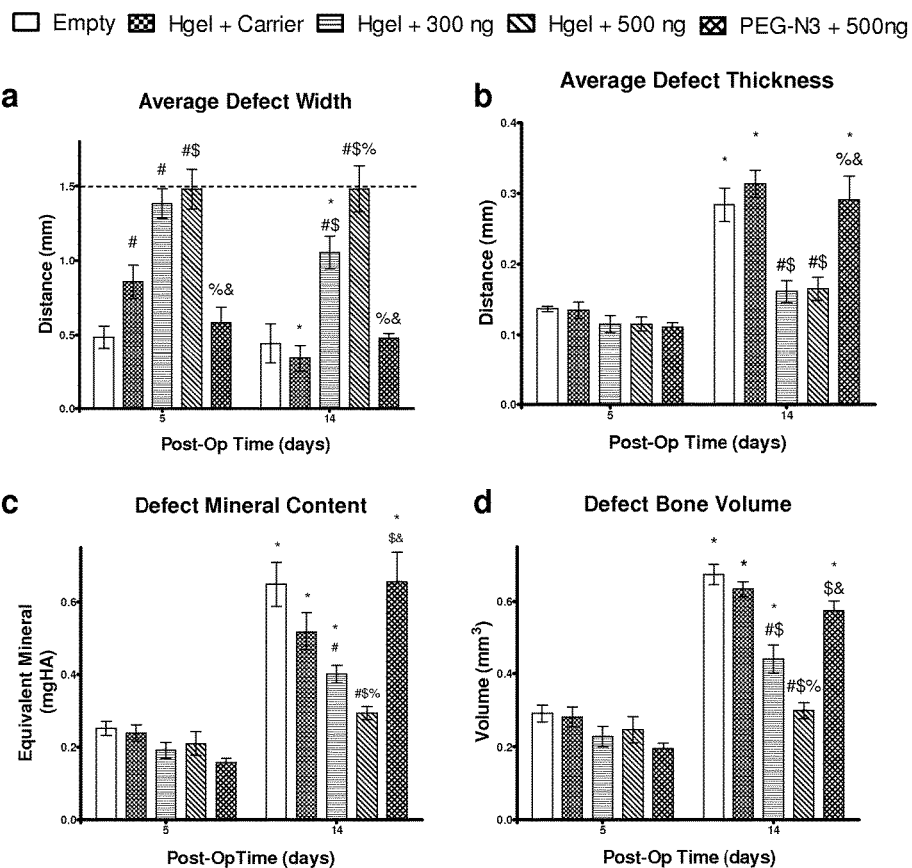
Figures 8 A-D

POLYMER HYDROGELS FOR IN VIVO APPLICATIONS AND METHODS FOR USING AND PREPARING SAME

CROSS-REFERENCE TO RELATED APPLICATIONS

This application is a US National Stage of International Application No. PCT/US2012/029686, filed 19 Mar. 2012, which claims the benefit of U.S. Provisional Patent Application No. 61/453,818, filed 17 Mar. 2011, both herein fully incorporated by reference.

TECHNICAL FIELD

The various embodiments of the present disclosure relate generally to polymer hydrogel compositions, methods of making polymer hydrogel compositions, and methods of using polymer hydrogel compositions. More particularly, various embodiments of the present disclosure are directed toward polymer hydrogels for in vivo delivery of biologically active materials in therapeutic treatments.

BACKGROUND OF THE INVENTION

The controlled release of a therapeutic agent is a central premise of medicine. The controlled release over time of a pharmaceutical drug is a recognized, if not completely predictable, technology that is available in numerous drugs currently on the market. While, controlled release often indicates the release of a compound over a period of time, e.g. the time release of a chemical compound, controlled release can also indicate the release of a compound at a specific location, e.g. drug delivery. Coated stent technology is an example of the delivery of a drug to the arterial area near the stent.

However, in contrast to the time release of simple chemical compounds or delivery of a drug in from a stent, the controlled release of recombinant proteins in vivo via injectable delivery vehicles remains a central challenge in drug delivery. PLGA-based injectable delivery vehicles for model proteins and peptides have been developed, but these delivery vehicles have not been able to deliver recombinant proteins because of their scarcity and fragility. As medicine continues to develop recombinant proteins for therapeutic uses, there will remain a need for delivery of those compounds.

Injectable hydrogels have been considered as a method for delivering drugs to a biological system. Hydrogels are composed of mutually reactive precursors that react in situ to form networks with high water content, mimicking mechanical and chemical properties of surrounding tissues. By varying the concentrations and chemical properties of the soluble precursors, mesh size, degradation times, mechanical properties and release rates of therapeutic agents might be controlled. Although various materials have been used to form synthetic injectable hydrogels, by far the most widely studied gels are those formed from macromolecular poly (ethylene glycol) (PEG) precursors. Numerous free radical polymerization mechanisms have been employed to generate hydrogel networks from soluble PEG-based precursors, but the initiators and free radicals produced during polymerization have the potential to damage the encapsulated therapeutic agents and surrounding tissues. Thus there remains a need to develop injectable hydrogels that are compatible with in vivo uses.

SUMMARY

Various embodiments of the present invention are directed compositions and uses of polymer hydrogels and the delivery of therapeutic agents in vivo. More particularly, various embodiments of the present disclosure are directed to a polymer hydrogel, which can include a polyacrylate backbone and a crosslinking member, methods of using the polymer hydrogel, methods of preparing the polymer hydrogel, and kits for the polymer hydrogel.

In an embodiment of the present invention, the polymer hydrogel can be a compound of Formula I.

Formula I

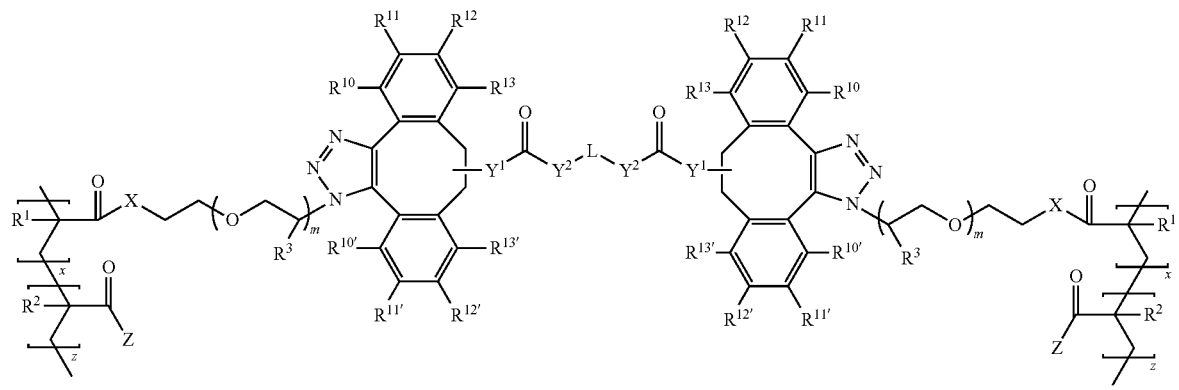

where $R^1$ and $R^2$ can each be independently hydrogen or a $C_1$ to $C_6$ hydrocarbon; $R^3$ can be hydrogen or methyl; X can be —O—, —S— or —NR$^5$—; Z is —OR$^6$, —SR$^6$, or NR$^5$R$^6$; m can greater than or equal to 1; x can be an integer greater than zero and z can be zero or an integer greater than zero; $R^5$ can be hydrogen or $C_1$ to $C_6$ hydrocarbon; $R^6$ can be hydrogen, $C_1$ to $C_6$ hydrocarbon or a polyglycol chain of two to ten glycol units; each $R^{10}$, $R^{11}$, $R^{12}$, $R^{13}$, $R^{10'}$, $R^{11'}$, $R^{12'}$, and $R^{13'}$ can independently be hydrogen, $C_1$ to $C_6$ alkyl, $C_1$ to $C_6$ alkoxy, nitro, fluoro, chloro, or bromo; $Y^1$ and $Y^2$ can each independently be —O—, —S—, or —NR$^4$— wherein $R^4$ can be hydrogen or a $C_1$ to $C_6$ hydrocarbon; and L can contain a polyglycol.

In an exemplary embodiment of the present invention, the polymer hydrogel can include a polyacrylate backbone of Formula II, Formula II

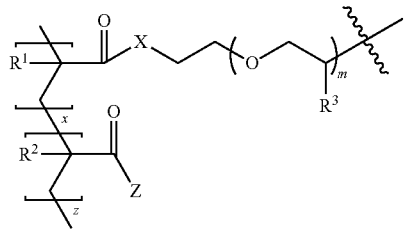

and a crosslinking member of Formula III

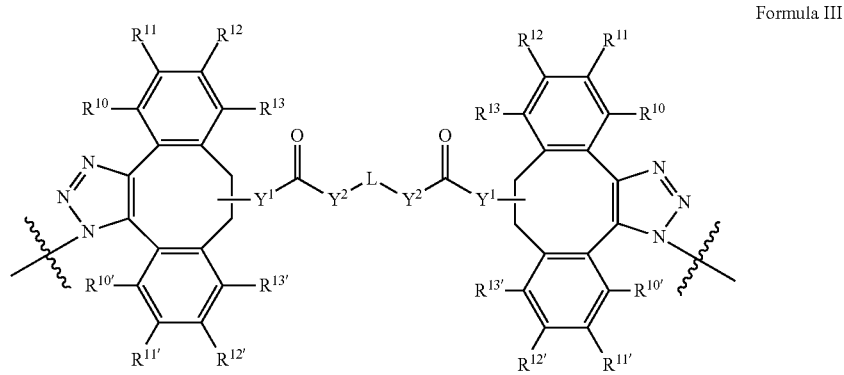

Formula III where $R^1$ and $R^2$ can each be independently hydrogen or a $C_1$ to $C_6$ hydrocarbon; $R^3$ can be hydrogen or methyl; X can be —O—, —S— or —$NR^5$—; Z is —$OR^6$, —$SR^6$, or $NR^5R^6$; m can greater than or equal to 1; x can be an integer greater than zero and z can be zero or an integer greater than zero; $R^5$ can be hydrogen or $C_1$ to $C_6$ hydrocarbon; $R^6$ can be hydrogen, $C_1$ to $C_6$ hydrocarbon or a polyglycol chain of two to ten glycol units; each $R^{10}$, $R^{11}$, $R^{12}$, $R^{13}$, $R^{10'}$, $R^{11'}$, $R^{12'}$, and $R^{13'}$ can independently be hydrogen, $C_1$ to $C_6$ alkyl, $C_1$ to $C_6$ alkoxy, nitro, fluoro, chloro, or bromo; $Y^1$ and $Y^2$ can each independently be —O—, —S—, or —$NR^4$— wherein $R^4$ can be hydrogen or a $C_1$ to $C_6$ hydrocarbon; and L can contain a polyglycol.

In an exemplary embodiment of the present invention, the polymer hydrogel can be prepared by the reaction of a polyacrylate azide of Formula IV

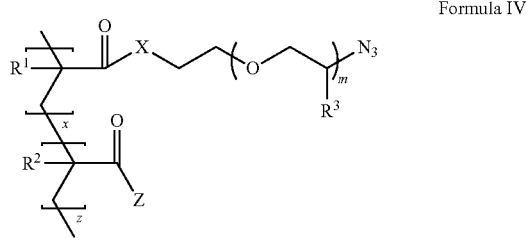

Formula IV with a crosslinking alkyne of Formula V

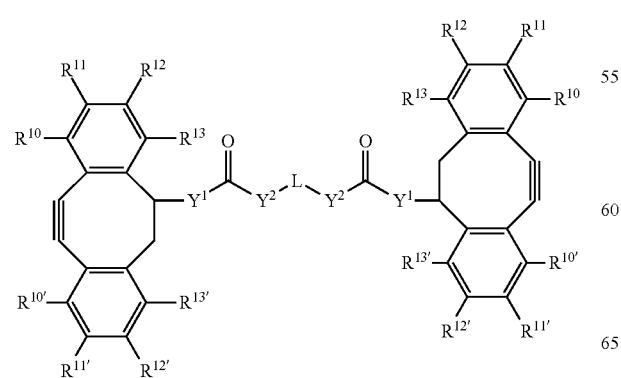

Formula V where $R^1$ and $R^2$ can each be independently hydrogen or a $C_1$ to $C_6$ hydrocarbon; $R^3$ can be hydrogen or methyl; X can be —O—, —S— or —$NR^5$—; Z is —$OR^6$, —$SR^6$, or $NR^5R^6$; m can greater than or equal to 1; x can be an integer greater than zero and z can be zero or an integer greater than zero; $R^5$ can be hydrogen or $C_1$ to $C_6$ hydrocarbon; $R^6$ can be hydrogen, $C_1$ to $C_6$ hydrocarbon or a polyglycol chain of two to ten glycol units; each $R^{10}$, $R^{11}$, $R^{12}$, $R^{13}$, $R^{10'}$, $R^{11'}$, $R^{12'}$, and $R^{13'}$ can independently be hydrogen, $C_1$ to $C_6$ alkyl, $C_1$ to $C_6$ alkoxy, nitro, fluoro, chloro, or bromo; $Y^1$ and $Y^2$ can each independently be —O—, —S—, or —$NR^4$— wherein $R^4$ can be hydrogen or a $C_1$ to $C_6$ hydrocarbon; and L can contain a polyglycol.

In an exemplary embodiment of the present invention, a kit for the treatment of an anatomical part of a body can include an aqueous solution of a polyacrylate azide of Formula IV, an aqueous solution of a crosslinking alkyne of Formula V, and an aqueous solution of a therapeutic agent. In a preferred embodiment, the anatomical part can be a bone.

In an exemplary embodiment of the present invention, a method for treating a condition on or near a bone can be administering to a site on or near the bone a therapeutic agent in a polymer hydrogel of Formula I or Formula VI

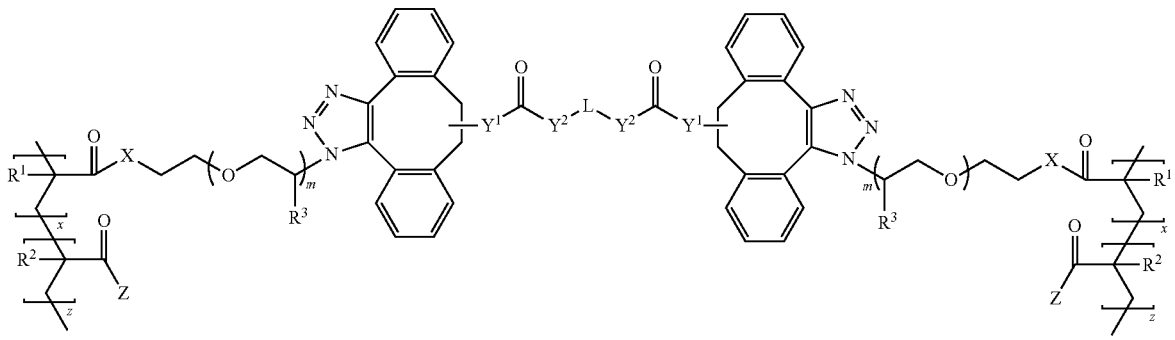

Formula VI where $R^1$ and $R^2$ can each be independently hydrogen or a $C_1$ to $C_6$ hydrocarbon; $R^3$ can be hydrogen or methyl; X can be —O—, —S— or —$NR^5$—; Z is —$OR^6$, —$SR^6$, or $NR^5R^6$; m can greater than or equal to 1; x can be an integer greater than zero and z can be zero or an integer greater than zero; $R^5$ can be hydrogen or $C_1$ to $C_6$ hydrocarbon; $R^6$ can be hydrogen, $C_1$ to $C_6$ hydrocarbon or a polyglycol chain of two to ten glycol units; $Y^1$ and $Y^2$ can each independently be —O—, —S—, or —$NR^4$— wherein $R^4$ can be hydrogen or a $C_1$ to $C_6$ hydrocarbon; and L can include a polyglycol.

BRIEF DESCRIPTION OF DRAWINGS

FIGS. 5 A-J illustrate in vivo fluorescence of a GST-647 in accordance with exemplary embodiments of the present invention.

FIGS. 6 A-C illustrate defect healing in a polymer hydrogel in accordance with exemplary embodiments of the present invention.

FIGS. 7 A-O illustrate μCT and histology for post operative samples in accordance with exemplary embodiments of the present invention.

FIGS. 8 A-D illustrate measurements of bone regeneration in accordance with exemplary embodiments of the present invention.

DETAILED DESCRIPTION

Figure 1A:
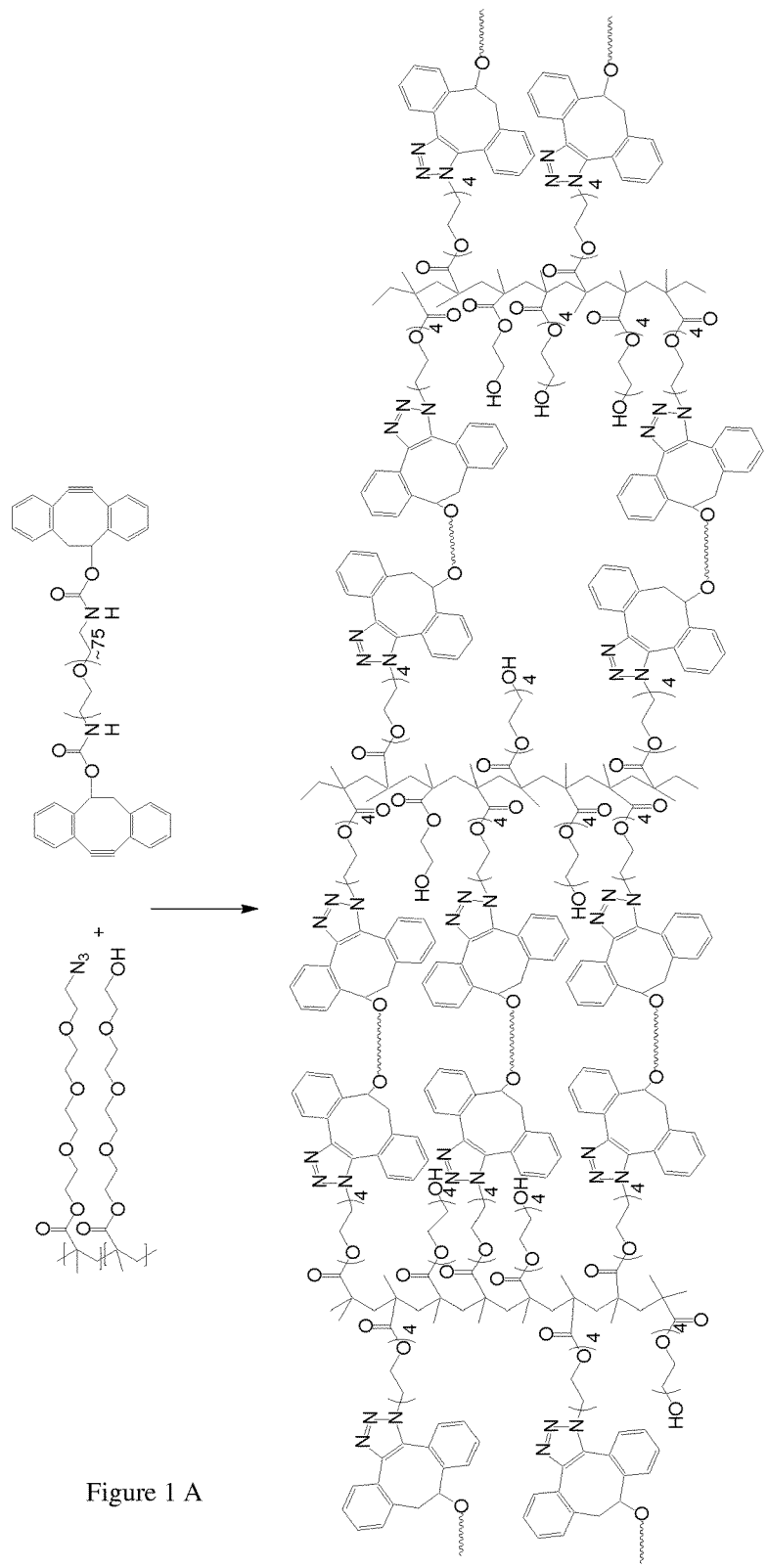
FIG. 1A illustrates a reaction to form a polymer hydrogel in accordance with exemplary embodiments of the present invention.
Figure 1:
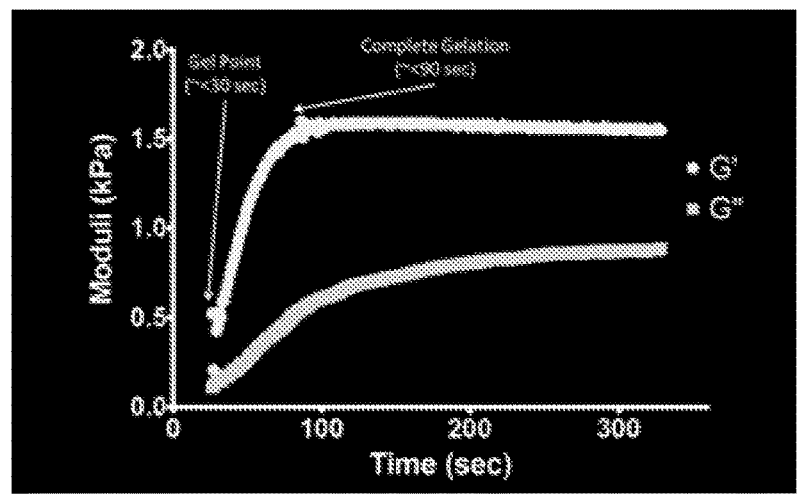
FIG. 1B illustrates a graph of the polymerization kinetics for a polymer hydrogel in accordance with exemplary embodiments of the present invention.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In this specification and in the claims that follow, reference will be made to a number of terms that shall be defined to have the following meanings:

As used herein, the term "substituted" is contemplated to include all permissible substituents of organic compounds. A substituent can include acyclic and cyclic, branched and unbranched, carbocyclic and heterocyclic, and aromatic and nonaromatic substituents of organic compounds. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. The terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "hydrocarbon" as used herein is any branched or unbranched covalently connected series of carbon and heteroatoms, which can be substituted or unsubstituted. The hydrocarbon can be fully saturated or unsaturated, and cyclic or acyclic. Categories of hydrocarbons include alkyls, alkenyls, alkynyls, aryls, alkoxys, and so forth.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and so forth. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. A "lower alkyl" group is an alkyl group containing from one to six carbon atoms.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkoxy" as used herein is an alkyl or cycloalkyl group bonded through a saturated carbon-oxygen single bond. "Alkoxy" also includes polymers of alkoxy groups as just described; that is, an alkoxy can be a polyether.

The term "alkenyl" as used herein is a hydrocarbon group of from 2 to 24 carbon atoms with a structural formula containing at least one carbon-carbon double bond. Both the E and Z isomers are considered, unless otherwise specified. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. "Cycloalkenyl" includes a cycloalkyl having at least one carbon-carbon double bond within the ring.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. "Cycloalkynyl" includes a cycloalkyl having at least one carbon-carbon triple bond within the ring.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted.

The terms "amine" or "amino" as used herein are moieties having a fully saturated nitrogen with three substituents that are independently, hydrogen or substituted or unsubstituted alkyl, cycloalkyl, alkenyl, cycloalkenyl, alkynyl, cycloalkynyl, aryl, or heteroaryl group described above. The term "carboxylic acid" as used herein is represented by the formula —C(O)OH. The term "halide" as used herein refers to the halogens fluorine, chlorine, bromine, and iodine. The term "hydroxyl" as used herein is represented by the formula —OH. The term "azide" as used herein is represented by the formula —$N_3$. The term "nitro" as used herein is represented by the formula —$NO_2$. The term "nitrile" as used herein is represented by the formula —CN.

The term "ester" as used herein is represented by the formula —OC(O)— can be a substituted or unsubstituted alkyl, cycloalkyl, alkenyl, cycloalkenyl, alkynyl, cycloalkynyl, aryl, or heteroaryl group described above. The term "amide" as used herein is represented by the formula —N—C(O)—, where the N is fully saturated. The term "carbonate" is represented by the formula —OC(O)O—, the term "carbamate" is represented by the formula —OC(O)N—, and the term "urea" is represented by the formula —NC(O)N—. Species that are alternately substituted at the —O— with an —S— will have the prefix "thio-" as recognized by those of skill in the art.

The term "ether" as used herein is represented by the structural moiety —C—O—C— where each C is independently a carbon of a hydrocarbon, such as a substituted or unsubstituted alkyl, cycloalkyl, alkenyl, cycloalkenyl, alkynyl, cycloalkynyl, aryl, or heteroaryl group as previously described.

The term "polyether" as used herein is a series of repeating ether units that are either the same or different from one another, and having a repeating unit that is an integer of from 1 to 500

The term "polyglycol" as used herein indicates a category of polyether compounds, and includes a repeating chain of substituted or unsubstituted polyethylene glycol units, including polyethylene glycol (PEG) (also called polyethylene oxide or PEO), polypropylene glycol (PPG) (also called polypropylene oxide or PPO) and other substituted polyethylene glycol. The term "glycol" as used herein indicates a subunit of the polyglycol, e.g. polyethylene glycol has a glycol subunit of —$CH_2$—$CH_2$—O—.

Reference will now be made in detail to specific aspects of the disclosed materials, compounds, compositions, articles, and methods, examples of which are illustrated in the accompanying Examples and Figures.

The present inventive composition can include a polymer hydrogel which can be described by the structure shown in Formula I:

Formula I

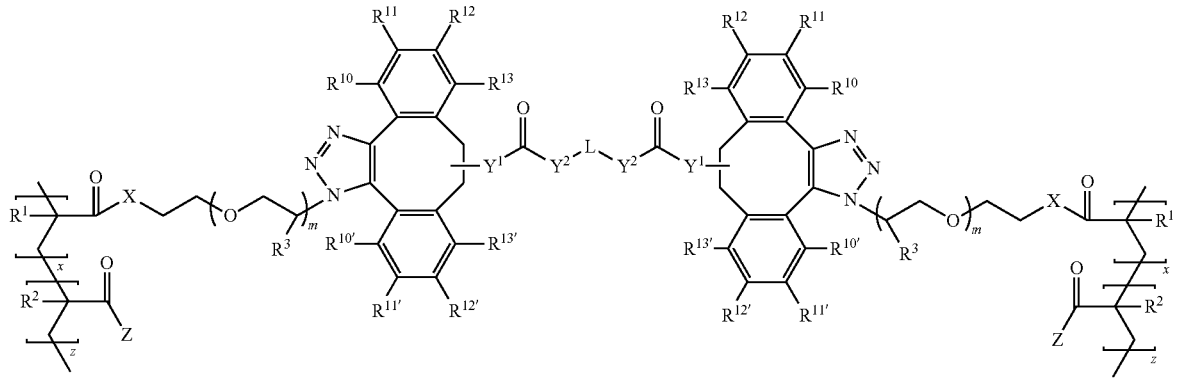

Alternatively, the polymer hydrogel can also be described by as having at least two parts, a polyacrylate backbone as shown by Formula II Formula II

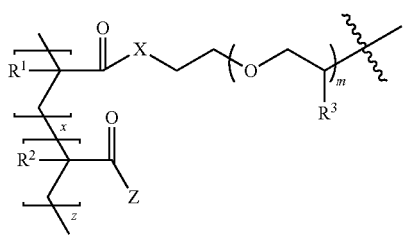

and a crosslinking member as shown by Formula III

Formula III

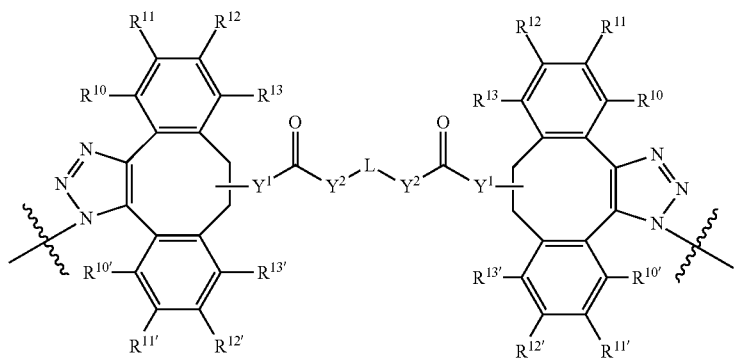

The polyacrylate backbone and the crosslinking member can be connected either directly or via an intervening substituent. In an exemplary embodiment, the crosslinking member and the polyacrylate are connected through the triazole ring.

In the polymer hydrogel as well as and its precursors and components as set forth throughout the specification herein, $R^1$ and $R^2$ can each be independently hydrogen or a $C_1$ to $C_6$ hydrocarbon, preferably hydrogen or methyl; $R^3$ can be hydrogen or methyl; X can be —O—, —S—, or —NR$^5$—, preferably O, and Z can be —OR$^6$, —SR$^6$, or NR$^5$R$^6$, preferably —OR$^6$; with $R^5$ as hydrogen or $C_1$ to $C_6$ hydrocarbon and $R^6$ as hydrogen, $C_1$ to $C_6$ hydrocarbon or a polyglycol chain of two to ten glycol units.

In the polymer hydrogel as well as its precursors and components as set forth throughout the specification herein, m can be an integer greater than or equal to 1, including between 1 and 20 inclusive, between 1 and 10 inclusive, greater than or equal to 2, between 2 and 10 inclusive, between 2 and 8 inclusive, between 2 and 6 inclusive, and between 3 and 6 inclusive.

In the polymer hydrogel as well as its precursors and components as set forth throughout the specification herein, each $R^{10}$, $R^{11}$, $R^{12}$, $R^{13}$, $R^{10'}$, $R^{11'}$, $R^{12'}$, $R^{13'}$ can independently be hydrogen, $C_1$ to $C_6$ alkyl, $C_1$ to $C_6$ alkoxy, nitro, fluoro, chloro, or bromo, preferably hydrogen or fluoro, or alternatively hydrogen only. $Y^1$ and $Y^2$ can each independently be —O—, —S—, or —NR$^4$— wherein $R^4$ can be hydrogen or a $C_1$ to $C_6$ hydrocarbon, and alternatively $Y^1$ and $Y^2$ can each independently be —O— or —NR$^4$, and preferably $Y^1$ can be O and $Y^2$ can be NH. Alternatively, $Y^1$ can be NH and $Y^2$ can be O.

In the polymer hydrogel as well as its precursors and components as set forth throughout the specification herein, L can contain a polyglycol, preferably a polyethylene glycol, a polypropylene glycol, or a mixture of a polyethylene glycol and a polypropylene glycol.

In the polymer hydrogel as well as its precursors and components as set forth throughout the specification herein, x can be an integer greater than zero; and z can be zero or an integer greater than zero. A ratio of x to z can be described when z is a non-zero integer. In an embodiment, the ratio of x to z can be less than or equal to about 50:1. The ratio of x to z can also be greater than or equal to about 1:10. In an embodiment, the ratio of x to z is between about 50:1 to about 1:5, alternatively about between about 10:1 to about 1:1. In an exemplary embodiment, the ratio of x to z can be between about 5:1 to about 2:1.

The polyacrylate backbone can be described as being formed by the polymerization of one or more of an acrylic acid compound, such as an acrylic acid, an acrylic ester, an acrylic amide, or the like. The acrylic acid compound may be substituted at any position on the alkene bond by one or more hydrocarbons, such as $H_2C\!=\!CH\!-\!C(O)\!-\!$, $RHC\!=\!CH\!-\!C(O)\!-\!$, $RR'C\!=\!CH\!-\!C(O)\!-\!$, $RR'C\!=\!CR''\!-\!C(O)\!-\!$, $RHC\!=\!CR'\!-\!C(O)\!-\!$, or $H_2C\!=\!CR\!-\!C(O)\!-\!$. Any monomer unit containing an acrylate or di-acrylate may be incorporated into the polymer backbone to generate a multifunctional polymer support for drug delivery and or cell attachment.

The polyacrylate backbone can be prepared from one or more different acrylic acid compounds. In an embodiment, the polyacrylate backbone can be formed from a single acrylic acid compound, and could be a compound of Formula VII:

Formula VII

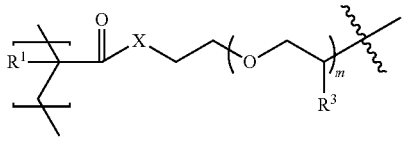

wherein $R^1$, $R^3$, X and m are as described above. In another embodiment, the polyacrylate backbone can be described as being formed by the polymerization of two acrylic acid compounds, and would be a compound of Formula II. One of ordinary skill in the art would recognize that the acrylic acid compounds would be randomly polymerized within the polyacrylate backbone. In yet another embodiment, the polyacrylate backbone can be described as being formed by the polymerization of three or more acrylic acid compounds, for example as shown for a compound of Formula VIII Formula VIII

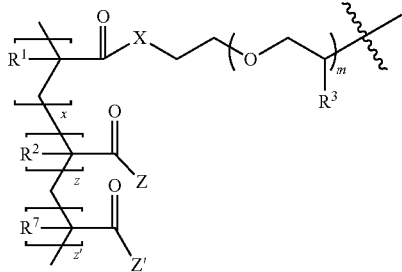

wherein $R^1$, $R^2$, and $R^7$ can each be independently hydrogen or a $C_1$ to $C_6$ hydrocarbon; $R^3$ can be hydrogen or methyl; Z and Z' can each independently be $-OR^6$, $-SR^6$, or $NR^5R^6$; m can be an integer greater than or equal to 1; x can be an integer greater than zero, z and z' can each independently be an integer greater than zero; $R^5$ can be hydrogen or $C_1$ to $C_6$ hydrocarbon; $R^6$ can be hydrogen, $C_1$ to $C_6$ hydrocarbon or a polyglycol chain of two to ten glycol units, ending in a free hydroxyl or a terminal $C_1$ to $C_4$ ether.

In an exemplary embodiment, the polyacrylate backbone can have an $R^1$ that can be hydrogen or methyl, an $R^2$ when present that can be hydrogen or methyl, and $R^7$ when present that can be hydrogen or methyl.

In an embodiment of the present invention, the polyacrylate backbone of the polymer hydrogel can have at least one polyglycol chain, described by the portion of the structure pendant to the X. i.e. $-OCH_2CHR^3-$, as exemplified in at least Formulas I and II. In an embodiment, the polyglycol chain can be described by the glycol repeating structure defined by m. In an embodiment, m can be an integer greater than or equal to 1. In an embodiment, m can also be less than or equal to 20. In an exemplary embodiment m can be from 2 to 20 inclusive, from 2 to 15 inclusive, from 2 to 10 inclusive, or from 2 to 8. In another exemplary embodiment, m can be from 3 to 10 inclusive, 3 to 8 inclusive, from 3 to 7 inclusive, or from 3 to 6 inclusive.

When the polyacrylate backbone contains two acrylate acid compound subunits, as in for example Formula I or II, Z can be $-OR^6$, $-SR^6$, or $NR^5R^6$ and $R^6$ can be hydrogen, $C_1$ to $C_6$ hydrocarbon or a polyglycol chain of two to ten glycol units. In an embodiment, $R^6$ can be hydrogen or $C_1$ to $C_6$ hydrocarbon. In another embodiment, $R^6$ can by a polyglycol chain of two to eight glycol units, or a polyglycol chain of three to six glycol units.

When $R^6$ is a polyglycol, then $R^6$ can end in a free hydroxyl, amine, terminal $C_1$ to $C_4$ ether, ester, amide, carbonate, carbamate, or urea, preferably a free hydroxyl or terminal ether, more preferably as a free hydroxyl.

When the polyacrylate backbone is prepared from at least two acrylic acid compounds, the polyacrylate backbone will include a ratio of the two acrylic acid compounds, which can also be described in at least Formulas I and II as a the ratio of x and z. In an embodiment, the ratio of x to z can be less than or equal to about 50:1. The ratio of x to z can also be greater than or equal to about 1:10. In an embodiment, the ratio of x to z is between about 50:1 to about 1:5, alternatively about between about 10:1 to about 1:5, or from about 10:1 to about 1:1. In an exemplary embodiment, the ratio of x to z can be between about 5:1 to about 1:1, or about 5:1 to about 2:1. In the case where the polyacrylate backbone is prepared with three or more acrylic acid compounds, as in Formula VIII above, z' is understood to be part of z for purposes of determining the ratio.

The polyacrylate backbone can include X as $-O-$, $-S-$, or $-NR^5-$ and Z as $-OR^6$, $-SR^6$, or $NR^5R^6$ when z is a non-zero integer. When X or Z are oxygens, the moiety can be described as an ester, and the acrylic acid compound that serves as a precursor would be described as an acrylate ester. When X or Z are nitrogens, i.e. $NR^5$, the moiety can be described as an amide and the acrylic acid compound that serves as a precursor would be described as an acrylate amide or acrylamide.

The crosslinking member can be a structure as shown by Formula III

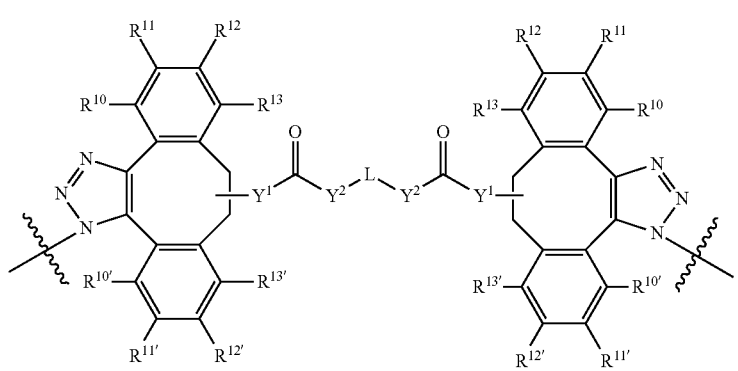

Formula III where each $R^{10}$, $R^{11}$, $R^{12}$, $R^{13}$, $R^{11'}$, $R^{11'}$, $R^{12'}$, $R^{13'}$ can each independently be hydrogen, $C_1$ to $C_6$ alkyl, $C_1$ to $C_6$ alkoxy, nitro, fluoro, chloro, or bromo; $Y^1$ and $Y^2$ can each independently be —O—, —S— or —NR$^4$— wherein R$^4$ can be hydrogen or a $C_1$ to $C_6$ hydrocarbon; and L can contain a polyglycol. The crosslinking member can be further described as generally having two subunits—a pair of triaza-bis-benzo-cyclooctenyl ring systems and a bridging polyglycol portion that also contain the carbonyl groups. Because each crosslinking member has two subunits composed of the triaza-bis-benzo-cyclooctenyl ring systems, each side can bind to a polyacrylate backbone portion. One of ordinary skill will recognize that the specific polyacrylate backbone that is bound on each end of the crosslinking member can be portions of the same polyacrylate molecule or can be from different polyacrylate molecules.

In a preferred embodiment, each of $R^{10}$, $R^{11}$, $R^{12}$, $R^{13}$, $R^{10'}$, $R^{11'}$, $R^{12'}$, $R^{13'}$ can be hydrogen. In an alternate embodiment, one or more $R^{10}$, $R^{11}$, $R^{12}$, $R^{13}$, $R^{10'}$, $R^{11'}$, $R^{12'}$, $R^{13'}$ can each independently be fluoro and the remaining can be hydrogen.

The combination of $Y^1$, $Y^2$ and the carbonyl group can be described as a carbonate when both $Y^1$ and $Y^2$ are oxygen, a carbamate when $Y^1$ or $Y^2$ is oxygen and the other is NR$^4$, or a urea, when both $Y^1$ and $Y^2$ are NR$^4$. In one embodiment, the combination of $Y^1$, $Y^2$ and the carbonyl group is a carbamate. In another embodiment, the combination of $Y^1$, $Y^2$ and the carbonyl group is a carbonate. In instances where a sulfur is present as either $Y^1$ or $Y^2$, the thio prefix can be applied. One advantage in these compositions is that the degradation of the polymer hydrogel can be modified based on chemical groups that are incorporated into these hydrogels. For example, the use of the carbonate with $Y^1$ and $Y^2$ each being oxygen allows for easier degradation and faster release than if one or both of $Y^1$ and $Y^2$ are nitrogens. In an exemplary embodiment, $Y^1$ is an O and $Y^2$ is NR$^4$.

In an embodiment of the present invention, the structure L can contain a polyglycol. The polyglycol can be composed of 10-1000 glycol subunits, 20-500 glycol subunits, or 20 to 200 glycol subunits. Alternatively, the polyglycol can be composed of 10-150 glycol subunits, 50-200 glycol subunits, or 75-350 glycol subunits. Determination of the polyglycol length can be varied depending on the application to which the polymer hydrogel is being applied. The polyglycol portion of L can also be described by a molecular weight number, $M_w$, of between about 500 and about 10000, between about 1000 and about 8000, or between about 1500 and about 7500. The glycol subunit can be an ethylene glycol, a propylene glycol, or a high alkyl glycol. In an embodiment, the glycol subunit is an ethylene glycol or a propylene glycol, preferably an ethylene glycol. The glycol subunit can also be a mixture of two or more glycols, for example ethylene glycol and a propylene glycol.

In an embodiment, the structure L can contain the polyglycol and one or more additional chemical moieties within the polyglycol chain. The structure L can include one or more additional chemical moieties that can be esters, amides, carbonates, carbamates, or ureas. For example, an L containing a polyethylene glycol and a carbonate structure might have a formula such as $[(CH_2CH_2O)_pC(O)O—]_q—$. Similarly, the unit could instead include carbamates, ureas, amides or esters, or a combination thereof. Including these moieties can allow further tailoring of the degradation or stability of the polymer hydrogel when used in a biological environment. Stimuli responsive units can also be incorporated into L, and would allow the hydrogels to degrade in response to cellular signals such as enzyme production or ph changes.

In Formula III, as well as several other formulas, the connectivity of $Y^1$ to the triazacyclooctene ring is not specified, due to the nature of the bond formation for the alkyne and azide, as discussed below. One of skill in the art would recognize that the two open carbon positions are not chemically equivalent, due to at least the relative position of the bond off of the triazole ring. In the polymer hydrogel, both of these positions might be occupied by the bond to $Y^1$ as shown below.

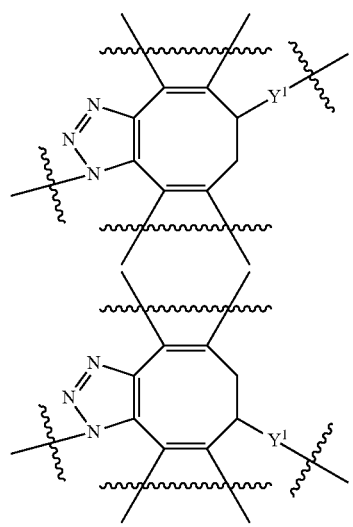

In an exemplary embodiment of the present invention, the polymer hydrogel can have a structure of formula IX Formula IX

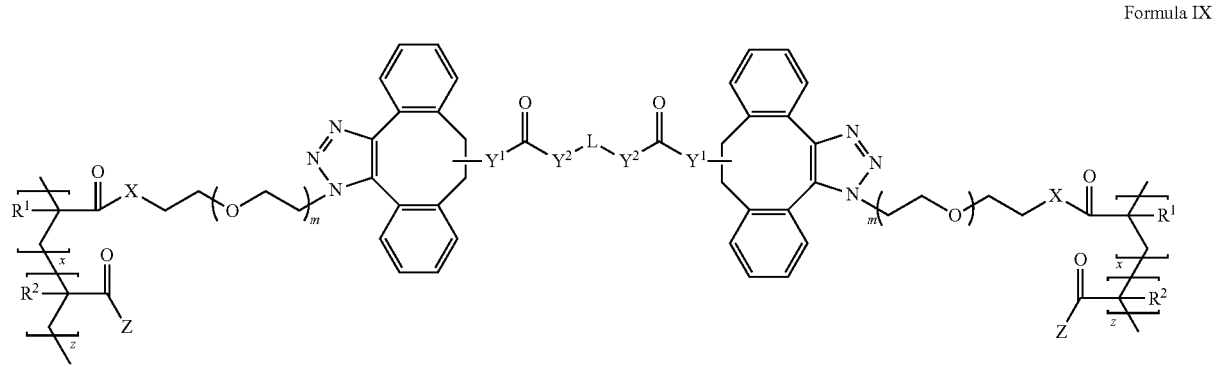

wherein, $R^1$ and $R^2$ are each independently hydrogen or a $C_1$ to $C_6$ hydrocarbon, x is an integer greater than zero, z is zero or an integer greater than zero, m is greater than or equal to 2, X is —O— or —NR—, Z is $OR^6$ or $NHR^6$, wherein $R^6$ is hydrogen, $C_1$ to $C_6$ hydrocarbon or a polyglycol chain of two to ten glycol units, $Y^1$ is —O—, $Y^2$ is —NH—, and L comprises a polyethylene glycol. In another embodiment, $R^1$ and $R^2$ are each independently hydrogen or methyl, x and z are integers greater than zero, X is O; $Y^1$ is —O—, $Y^2$ is —NH—, and Z is $OR^6$, wherein $R^6$ is a polyethylene glycol of two to ten ethylene glycol units, and L comprises a polyethylene glycol of 10 to 100 ethylene glycol units.

The polymer hydrogels of the present invention can be formed by a [3+2] cycloaddition reaction between an alkyne and an azide. In a embodiment, a method of making the polymer hydrogels can include the reaction of a polyacrylate azide of Formula IV Formula IV

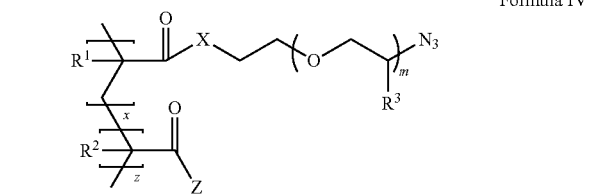

and a crosslinking alkyne of Formula V

Formula V

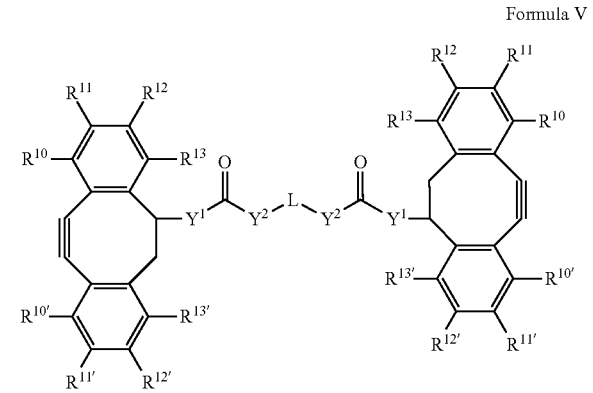

where $R^1$, $R^2$, $R^3$, X, m, x, z, $R^{10}$, $R^{11}$, $R^{12}$, $R^{13}$, $R^{10'}$, $R^{11'}$, $R^{12'}$, $R^{13'}$, $Y^1$, $Y^2$ and L are as defined above. The reaction can be conducted in aqueous solution. The reaction and the resulting polymer hydrogel do not require or contain a metal salt, particularly a copper salt.

This two component system contains the alkyne and the azide which upon mixing react via a [3+2] cycloaddition to form a triazole ring that covalently crosslinks the components and forms the polymer hydrogel. Significantly, this reaction, commonly described as click chemistry, does not require a metal catalyst. Traditional reactions involving similar [3+2] cycloadditions have relied on a catalyst, typically CuI to undergo reaction at any significant rate. The classical Cu-catalyzed Huiseng cyclo-addition has been used to crosslink azide and alkynes, but the toxicity associated with the copper catalyst diminishes the clinical viability of such systems. Recently a copper-free [3+2] cycloaddition of a hydrogel composed of an azide-terminated PEG and a polypeptide functionalized with difluorinated cyclooctyne was demonstrated. However, that reaction took approximately one hour to achieve complete polymerization. In comparison, the polymer hydrogels of the present invention can achieve gelation in less than thirty seconds and completely polymerize in less than ninety seconds due at least in part to the ring-strain associated with the dibenzocyclooctynyl ring. Thus, the present reaction is nearly two orders of magnitude faster. The resulting triazole ring connects the polyacrylate azide and the crosslinking alkyne to produce the polymer hydrogel at rates that are much more useful for biological applications. Moreover, the reaction occurs in aqueous conditions, making it very valuable for in vivo biological applications, and the rapid reaction can rapidly encapsulate co-administered therapeutic agents before they can diffuse away from an injection site.

In an embodiment of the present invention, compositions for the polymer hydrogel containing the an crosslinking alkyne and a polyacrylate azide can reach complete polymerization in less than about 3 minutes, preferably less than about 2 minutes, and more preferably less than about ninety seconds. In an embodiment of the present invention, compositions for the polymer hydrogel containing the an crosslinking alkyne and a polyacrylate azide can achieve gelation in less than about 1 minute, preferably less than about 45 second, and more preferably less than about 30 seconds. The complete polymerization and gelation are terms understood by one of ordinary skill in the art, and are a measureable value using standard techniques. The polymer hydrogels can achieve gelation and polymerization in these time frames either in vitro or in vivo, making the polymer hydrogels very effective in a clinical setting.

Because of the rapid gelation and polymerization of the polymer hydrogel of the instance invention, therapeutic agents can be included in the polymer hydrogel for treatments in a biological system. Therapeutic agents can include biologically active agents, biological agents, macromolecules, therapeutic molecules, and similar compounds as one of ordinary skill in the art would recognize. This may also include proteins, peptides, nucleic acids, or other small molecules. In an embodiment of the present invention, a therapeutic agent can be present in the compositions containing polymer hydrogel. The therapeutic agent can be encapsulated or absorbed in the polymer hydrogel. The therapeutic agent need not be chemically bonded to the polymer hydrogel. In an exemplary embodiment, the composition can contain a protein or nucleic acid, preferably a protein. The composition can contain a protein that is between about 5 to 100 kDa, or about 10 to about 50 kDa, or about 15 to about 35 kDa. Alternatively, the composition can contain as a therapeutic agent a pharmaceutical drug, commonly termed small molecule to distinguish from macromolecules. In an exemplary embodiment, the therapeutic agent can be included with the components that form the polymer hydrogel prior to the [3+2] cycloaddition. Thereby, the therapeutic agents can be delivered by the polymer hydrogel, or the polymer hydrogel can localize the therapeutic agents to a specific location. Moreover the polymer hydrogel can also be used as a scaffold to deliver or incorporate cells to a specific location.

Because of the nature of the polymer hydrogel synthesis and its synthetic components, an embodiment of the present invention can be a kit for a therapeutic treatment, where the kit contains an aqueous solution of a polyacrylate azide such as Formula IV above, an aqueous solution of a crosslinking alkyne such as Formula V above, and an aqueous solution of a therapeutic or biologically active agent. In an embodiment, the polyacrylate azide the kit can be a structure of Formula X

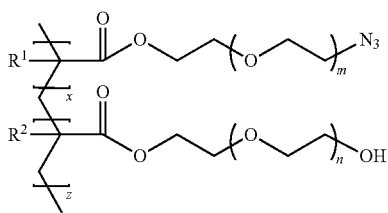

Formula X wherein $R^1$ and $R^2$ are each independently hydrogen or methyl, m is an integer between 1 and 20, n is an integer between 1 and 20, and x and z are as defined above. In an embodiment, m and n can each independently be an integer greater than or equal to 1, including between 1 and 20, inclusive, between 1 and 10 inclusive, greater than or equal to 2, between 2 and 10 inclusive, between 2 and 8 inclusive, between 2 and 6 inclusive, and between 3 and 6 inclusive.

In an embodiment, the crosslinking alkyne in the kit can be a structure of Formula XI

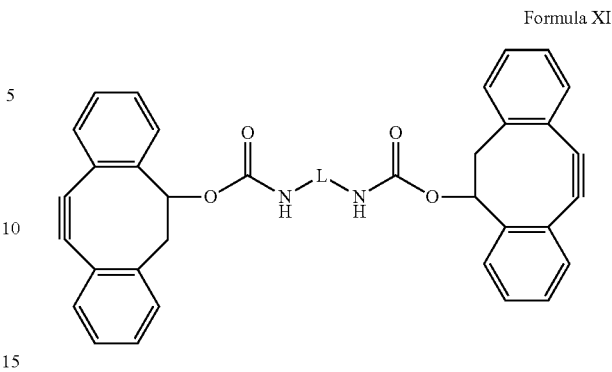

Formula XI where L is as defined above. In another embodiment, the crosslinking alkyne in the kit can be a structure of Formula XII

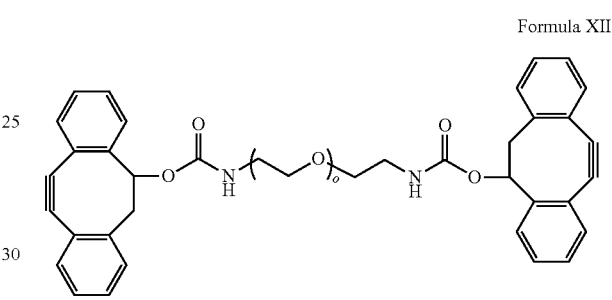

Formula XII wherein o is an integer between 10-100.

In an embodiment, the aqueous solution of the crosslinking alkyne can contain about 0.5% to about 20% w/v alkyne in water, preferably about 1% to about 15% w/v of alkyne in water, and more preferably about 1.5% to about 12.5% w/v of alkyne in water.

The compositions containing the polymer hydrogel can contain a substantial amount of water, as typical of hydrogels. This water content provides the polymer hydrogel with it ability to deliver therapeutic agents to a location while still maintaining its structure and characteristics. In an embodiment, the polymer hydrogel can have a concentration in water of between about 0.5% and 25%, preferably between about 1% and about 20%, more preferably between about 1.5% and about 15%, and even more preferably between about 1.5% and about 12.5%, all expressed in w/v of the polymer hydrogel in water.

Compositions of the polymer hydrogel can have numerous biological applications. In an embodiment, the polymer hydrogel can be used for aiding the healing or therapeutic treatment of a tissue, such as, for example, skin tissue, muscle tissue, bone, and any other biological area that can benefit from the localized and/or controlled delivery of a therapeutic agent. Moreover, the polymer hydrogels are tunable due to the different portions of the structure. Sections that can be varied include at least the polyglycol, which can be varied in length and glycol unit; the nature of the polyacrylate, by for example increasing or decreasing the portion of azide present to increase or decrease the amount of crosslinking in the hydrogel; varying the composition of the non-crosslinking portion of the polyacrylate to vary the environment within the gel; and so forth. With these tunable controls, the characteristics of polymer hydrogels can be changed to, for example, make the polymer hydrogel stiffer or more flexible, thereby matching the characteristics of the tissue to which it is being applied.

By way of example, the compositions having polymer hydrogel can be used to control the healing of bone defects, which are some of the most frequent and difficult challenges in medicine. These compositions can provide an in-situ polymerizing drug delivery scaffold for the modulation of bone healing. The therapy can designed for both long bone and calvaria defects, and can also be applied to a wide range of other applications.

In an exemplary embodiment of the present invention, the compositions of having the polymer hydrogel can be used to treat craniosynostosis. Craniosynostosis is the premature fusion of the cranial suture early in development. If left untreated it can lead to blindness, deafness, and developmental delays. The current treatment for more severe cases is the surgical removal of the fused suture and/or remodeling of the skull. In up to 40% of these surgeries the skull re-fuses prematurely, necessitating a second surgery to correct the re-fusion. This second surgery is associated with an incredibly high incidence of morbidities and mortalities. Despite the clinical need for a therapy to delay the healing of the cranial defect there is no therapy to delay the re-closure.

The polymer hydrogel disclosed herein can address these limitations by providing a tunable biodegradable scaffold to provide a controlled release of proteins, peptides, nucleic acids, or other small molecule to delay the formation of bone. In an embodiment of the present invention, the compositions can be used to deliver of proteins or their corresponding peptides to inhibit osteoblast differentiation such as, but not limited to, Noggin, Gremlin 1, and Sclerostin. Previous research has shown that the mineralization of this defect was associated with an increase in mRNAs for bone morphogenic protein (BMP) 2 (Bmp2), BMP-4 (Bmp4), and the BMP inhibitor Gremlin1 (Grem 1). BMP inhibitors like Gremlin1 are normally secreted to bind to their respective targets extracellularly as part of a negative feedback control system. As a result, these inhibitors are attractive therapeutic agents as they can alter BMP-dependent intracellular signaling without having to cross the cell membrane.

The polymer hydrogel based therapy disclosed herein can be designed to provide a delivery vehicle for proteins or other factors for craniosynostosis. One of the advantages of this polymer hydrogel is that it spontaneously polymerizes without the production free radicals or the need for metal catalysts such as copper, which is of particular concern in this application. There are no chemical solvents or initiators involved in the polymerization. The polymer hydrogel also has the advantage that the two components can be injected as liquids and polymerize in-vivo. This polymerization can take place in saline as well as in environments that contain blood.

The invention can also be used as a delivery vehicle for the promotion of long-bone or calvarial defects. This may be accomplished by the delivery of proteins, peptides, nucleic acids, or other small molecules. The polymer hydrogel can also be used as a cell delivery scaffold. This can be performed with either encapsulated cells or incorporation of the cells in a larger scaffold. The polymer has also been functionalized with the RGB peptide to deliver BMP2 and deferoxamine. The deferoxamine is a drug that up-regulates HIF which is associated with a pro-angiogenic response. The polymer hydrogel can also serve as a scaffold for other molecules to promote osteoblast differentiation that include but are not limited to BMP4, BMP7, etc. Additionally, the polymer hydrogel could include other pro-angiogenic factors designed to promote bone in-growth into the scaffold, such as but not limited to VEGF.

Thus, in an embodiment of the present invention, the therapeutic agent can be an agent that is used to treat bone, bone tissue, or an area near bone tissue. The therapeutic agent can be an agonist, antagonist, inhibitor or activator of enzymes or biological processors related to bone growth and development. The therapeutic agent can target the regulation of the BMP family of proteins, particularly an inhibitor or antagonist of BMP. In one exemplary embodiment, the compositions and methods containing the polymer hydrogel can include a recombinant protein that inhibits BMP, preferably a recombinant proteins of Gremlin, Noggin, or Sclerostin. In an alternative embodiment, the polymer hydrogel can deliver a therapeutic agent that aids and encourages bone growth and development. In one exemplary embodiment, the composition can contain deferoxamine.

While the polymer hydrogel can be used for craniofacial and orthopedic applications, there are numerous other uses. The polymer hydrogel can serve as a scaffold for delivery of bioactive molecules for dental applications to regenerate lost bone. The polymer hydrogel can also be used to deliver antibiotics to treat osteomyleitis, open skin ulcers, or other infections. The polymer hydrogel has also serve as a scaffold for the repair of large muscle defects or crush injuries, particularly where delivery of a localized therapeutic agent is desired for the treatment.

Thus, in another embodiment of the present invention, a therapeutic agent can be administered to an anatomical part of the body that would benefit from localized delivery of the therapeutic agent.

The various embodiments of the present invention are further illustrated by the following non-limiting examples.

Examples

Synthesis of Polymer Hydrogel

Synthesis of poly[Tetraethylene glycol methacrylate)-co-(azidotetraethylene glycol methacrylate)] (PEG-N3) was prepared by combining tetraethylene glycol methacrylate (0.9 g, 3.43 mmol) and azido tetraethylene glycol methacrylate (0.28 g, 1.0 mmol), micro RAFT agent (benzothioylsulfanyl)acetic acid (6.27 mg, 0.03 mmol), and AIBN (0.5 mg, 0.003 mmol) in dimethylformamide (1.5 ml). The reaction flask was degassed by five freeze-pump-thaw cycles, and then immersed in an oil bath and stirred at 70° C. After 20 h, the reaction was terminated by flash freezing the in liquid nitrogen. The reaction product was added to DCM (5 ml) and then precipitated from methanol (25 ml). The supernatant was decanted and the precipitated polymer was subjected to three more rounds of resuspension and precipitation before being concentrated under reduced pressure. The purified polymer was analyzed for weight by gel permutation chromatography (tetrahydrofuran) and the structure and purity were verified by $^1$H NMR (deuterated chloroform).

Figure 2:
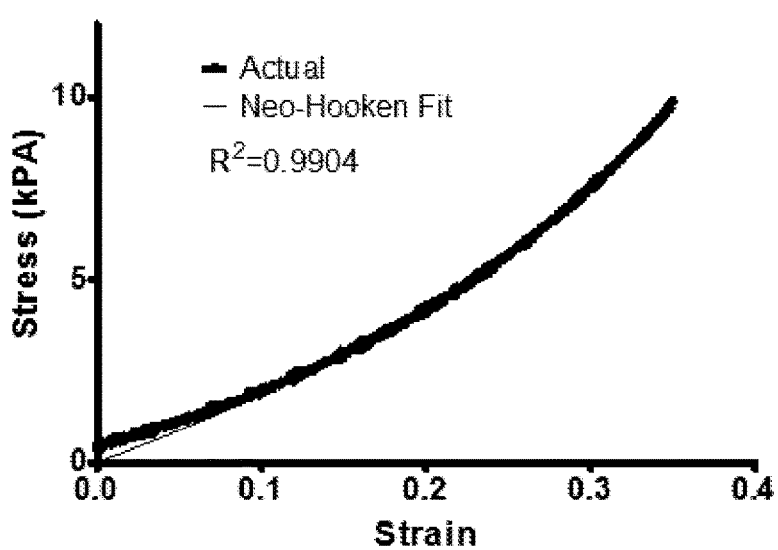
FIG. 2 illustrates a stress-strain curve for a developing polymer hydrogel in accordance with exemplary embodiments of the present invention.

Varying the relative concentration of a dibenzocyclooctynyl compound ("DBCO-PEG") analogous to Formula XII, where L is a polyethylene glycol having approximately 75 ethylene glycol units prior to polymerization allowed for the formation of gels with highly customizable properties. FIG. 1A shows the reaction of a polyacrylate azide (PEG-N3) with a DBCO-PEG, a crosslinking alkyne, to form a 3D ideal network hydrogel. Aqueous stock solutions of DBCO-PEG (12.5%, 6.25%, 4.85%, 3.13%, 1.56%; w:v) and PEG-N3 (50%; w:v) were used to form cylinders for unconstrained compression testing. Spinning disk rheometry showed that when the DBCO-PEG and PEG-N3 solutions were combined the gel point occurred in less than 25 seconds and complete polymerization occurred in less than 90 seconds, as shown in FIG. 1B. As with most hydrogels, the gel displayed a highly non-linear behavior in response to compression, which makes assumptions used with traditional engineering materials invalid. The Neo-Hookean hyperelastic constitutive equations were able to accurately model the stress-strain response of the gels, as shown in FIG. 2. The gel has random polymerization and has a relatively high water content, which allows for the assumption that the gels are both isotopic and incompressible. These assumptions allow the original constitutive equations to be simplified and allow the Neo-Hookean coefficient ($C_1$) to be found in terms of the stretch ratio ($\lambda$) and the engineering stress in the axial direction ($\sigma_{1i}^{eng}$):

$$\sigma_{11}^{eng} = 2C_1\left(\lambda - \frac{1}{\lambda^2}\right).$$

Figure 3:
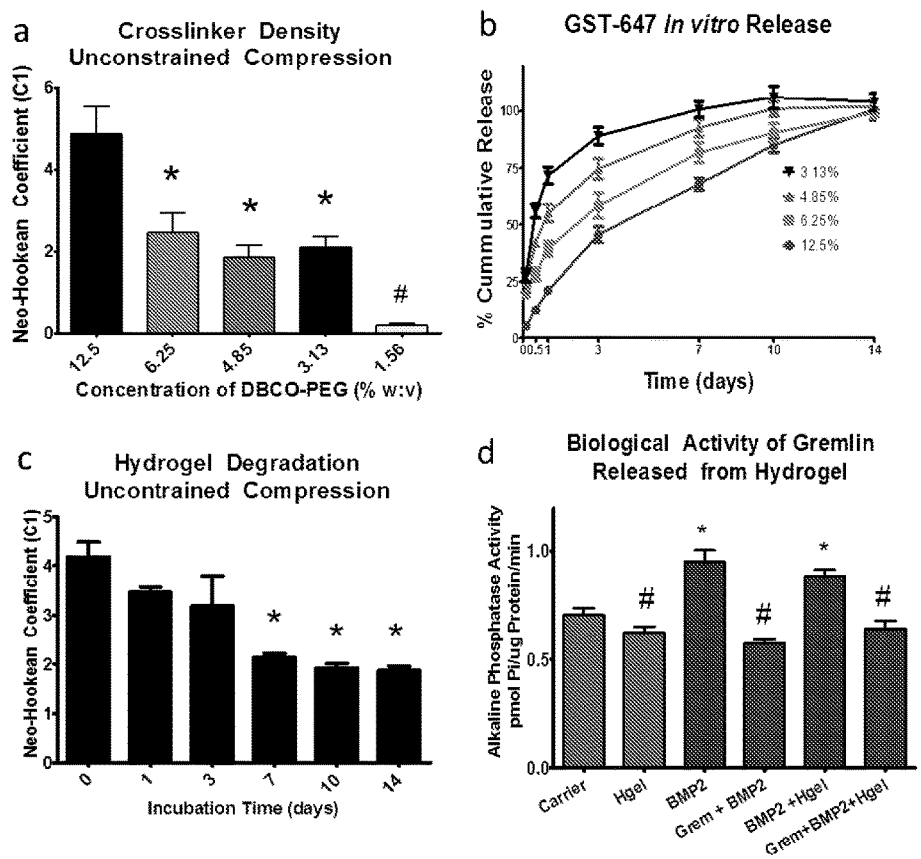
FIGS. 3 A-D illustrate graphs for in vitro testing of a polymer hydrogel in accordance with exemplary embodiments of the present invention.

Unconstrained compression testing showed that increasing the concentration of the DBCO-PEG resulted in an increase in the mechanical properties of the polymer hydrogel. FIG. 3A show the Unconstrained compression testing of hydrogel using a Neo-Hookean hyperelastic model showed that increasing the concentration of the DBCO-PEG resulted in an increase in the Neo-Hookean coefficient (C1). *=p<0.05 vs 12.5%. FIG. 3B shows the in vitro release of GST-647 from hydrogels with increasing concentrations of DBCO-PEG that resulted in a more prolonged and linear release profile with the 12.5% gel having controlled release out to 14 days. FIG. 3C shows that degradation of the 12.5% gel assessed by unconstrained compression had a decrease in the Neo-Hookean coefficient after day 7. *=p<0.05 vs day 0. FIG. 3D shows that the biological activity of rmGremlin1 was retained after release following polymerization in the hydrogel as assessed by blocking the rhBMP-2 mediated increase in alkaline phosphatase specific activity *=p<0.05 vs carrier, #=p<0.05 vs rhBMP2

At the lowest concentration, the Neo-Hookean coefficient was less than 0.3 then increased to approximately 2 for the mid concentrations, and then finally peaked at over 5 for the 12.5% DBCO-PEG (FIG. 3A). For the 12.5% gel this corresponds to a Young's modulus of approximately 32 kPA. Hydrogels with concentrations less than 1.5% or greater than 12.5% did not polymerize (data not shown). Increasing the concentration of the DBCO-PEG also resulted in a more linear and prolonged release of incorporated proteins.

Release Kinetics

In order to assess release kinetics, prior to polymerization, 12.5% hydrogels were loaded with glutathione s-tranferase (GST) labeled with an Alexa fluor carboxylic acid fluorophore (GST-647) as a model protein. This GST-647 complex has a molecular weight that is nearly identical to that of the BMP inhibitor Gremlin dimer. GST-647 loaded hydrogels were incubated for up to two weeks in sterile PBS with 10% FBS at 37° C. Measuring the total fluorescent signal showed that 12.5% hydrogels with the greatest concentration of cross-linker had the slowest release of GST-647 at all time points examined (FIG. 3B). Hydrogels with progressively lower cross-linking concentrations had a more rapid and non-linear release of incorporated protein with the 3.1% gel releasing nearly 75% of the protein after only 1 day while the 12.5% gel released 75% of proteins out to 10 days (FIG. 3B). The degradation of the 12.5% hydrogel showed that the compressive moduli were retained for 3 days of incubation, before gradually decreasing for the remaining time points (FIG. 3C).

In Vitro Testing

Figure 4:
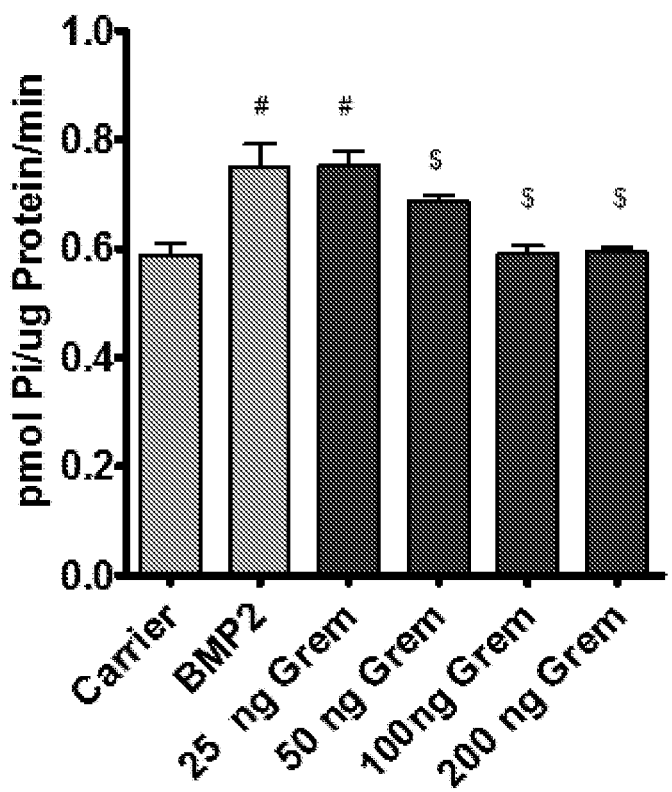
FIG. 4 illustrates a chart of dose response of a recombinant Gremlin1 in accordance with exemplary embodiments of the present invention.

Experiments using rmGremlin were performed to verify that proteins released from the polymer hydrogel can retain their biological activity following in situ polymerization. Gremlin is a traditional BMP antagonist and blocks the activity of BMP-2, BMP-4, and BMP-7. A conditioned media model was established in which pre-osteoblastic MG63 cells were treated with rhBMP2 and their differentiation monitored as a function of increased alkaline phosphatase specific activity. A preliminary dose-response study showed that 100 ng/mL rmGremlin1 was able to block the effect of rhBMP2 on this cell line. FIG. 4 shows that the dose-dependent effects of rmGremlin1 on ability of rhBMP2 to induce the differentiation of MG63 cells (rhBMP2 was added when cells were 80% confluent). There was an increase in alkaline phosphatase specific activity in response to rhBMP2 and this effect was blocked by the addition of rmGremlin1 in a dose dependent fashion. #=p<0.05 vs Carrier, $=p<0.05 vs BMP2. and that it was necessary to incubate hydrogels containing 100 ng/mL rmGremlin1 in the culture medium for 7 days to achieve release of the incorporated protein. Accordingly, hydrogels containing either rmGremlin1 or the vehicle control were incubated in the co-culture dishes for 7 days, at which time 100 ng/mL rhBMP2 was added to the well. Enzyme activity was measured 24 hours later. Cells treated with rhBMP2 alone or with the polymer hydrogel containing the rmGremlin1 vehicle (4 mM HCl) exhibited a 20% increase in alkaline phosphatase activity over control cultures, as shown in FIG. 3D. However, if rmGremlin1 was either injected into the medium or was released from the polymer hydrogel following in situ hybridization, the rhBMP1-dependent stimulation was reduced to control levels, as shown in FIG. 3D.

In Vivo Release Kinetics and Defect Healing

After verifying that the polymer hydrogel can provide controlled release of proteins that retain their biological activity following in situ polymerization, the in vivo release kinetics of a polymer hydrogel were assessed in the infant PF suture defect model. Following creation of the defect over the PF suture in 21 day old pups, mice were randomized for a 2 μL injection of either GST-647 in un-polymerized PEG-N3 or with the 12.5% hydrogel containing GST-647. For the latter experimental group, equal volumes of PEG-N3, DBCO-PEG, and the GST-647 were chilled on ice, mixed rapidly, and then injected into the defect. As the gels have a low viscosity prior to polymerization, the solution was able to fill the entire defect and then rapidly polymerize in situ, creating a stable gel in less than 90 seconds.

FIGS. 5 A-J show the in vivo fluorescence release of GST-647 kinetics following in situ polymerization of hydrogel. Fluorescent image of mice with GST-647 in cross linked hydrogel showed a controlled and localized signal over the defect out to 14 days post-op, as shown in FIGS. 5 A-D. In contrast the signal of the group containing the un-polymerized PEG-N3 showed that the protein rapidly diffused out of the defect and there was very little signal after post-op day 5, as shown in FIGS. 5 E-H. Quantification of the total fluorescent signal over the entire head shows that after day post-op day 2 there is more signal in the hydrogel gel group and there is only a slight decrease in the total fluorescent signal, as shown in FIG. 5 I, *=p<0.05 vs day 2, #=p<0.01 vs hydrogel. Comparing the ratio between the fluorescent signal in the defect to the total signal showed that the hydrogel groups had a higher value for post-op days 2 to 14, indicating that the hydrogel had a more controlled release of incorporated protein, as shown in FIG. 5 J, *=p<0.05 vs day 0, #=p<0.05 vs hydrogel.

When the polymer hydrogel was injected in the defects for in situ polymerization, the fluorescent signal remained localized within the site of the defect for all time points and decreased gradually over time (FIGS. 5 A-D). In contrast, the fluorescent signal in animals containing the un-polymerized PEG-N3 showed that the protein diffused out of the defect by 2 days post-op and there was essentially no signal seen on days 5 and 14 post-op (FIGS. 5E-H). Quantification of the total fluorescent signal over the entire head of the animals showed no differences for the first two time points, but there was less signal in the PEG-N3 mice for the later time points on post-op days 5 and 14 (FIG. 5 I). Additionally, the ratio between of signal contained within the defect to the total signal detected was approximately 1 for the polymer hydrogel groups, indicating that essentially all of the fluorescent proteins were localized to the defect (Figure F J). The groups containing just the un-polymerized PEG-N3 began at a ratio of approximately 1, but this more than doubled for the remaining time points as the proteins continued to diffuse away from the defect site.

To verify that the in situ polymerization of the polymer hydrogel was not toxic to the surrounding tissues, mice were randomized to have an empty cranial defect or injected with the polymer hydrogel containing PBS only. The extent of bone regeneration was imaged by micro-computed tomography (μCT) on post-operative days 2, 5, and 14 and the images quantified using advanced image processing algorithms developed by us previously to segment bones of varying and heterogeneous mineral content that are seen in the healing of the pediatric specific model 21. FIG. 6 A shows that at 5 days post-op there was a slight decrease in the defect width in the empty defect, but there were no difference on day 14. FIGS. 6 B and C show that In groups with the hydrogel there was slightly less total mineral content and bone volume on both post-op days 2 and 5 but no differences by post-op day 14. *=p<0.05 vs empty.

There was a transient reduction in the bone within defect treated with polymer hydrogel alone. By 14 days post-op there were no differences in either the average defect width or the volume of bone in the defect. This indicates that the polymer hydrogel has a space occupying effect early, but that in vivo the gel is degraded or replaced by the regenerating bone.

Polymer Hydrogel to Inhibit Re-Synostosis

The hydrogels are able to provide a highly localized, controlled delivery of incorporated proteins in vivo and do not have a long term impact on bone regeneration. To demonstrate that incorporated proteins can have a biological effect in vivo, the polymer hydrogel was used to delay post-operative bone growth following PF suturectomy by delivering the BMP inhibitor rmGremlin1 in a cranial defect model. Re-synostosis following suturectomy of the PF suture in infant mice is associated with an increase in expression of mRNAs for Bmp2, Bmp4 and Grem. In addition, Gremlin it has been previously shown to be more specific against BMP2 and BMP4 than other antagonists. Cranial defects were created in 21 day old mice (5 mice per group per time point) and randomized to both the post-operative time point and whether the defect contained one of the following treatments: empty defect, hydrogel+vehicle, hydrogel+300 ng rmGremlin1, hydrogel+500 ng rmGremlin1, un-polymerized PEG-N3+500 ng rmGremlin1. Mice were euthanized and imaged with μCT and decalcified histology on post-op days 5 and 14.

Empty defects contained a very thick trabeculated structure that was visible on both the μCT and histology images at 14 days post-op. The defects were nearly completely bridged as shown in the 3D rendering, similar to what was observed previously, as shown in FIGS. 7 A-C. Defects containing the polymer hydrogel had this same thick trabecular structure, but there was not complete bridging at the center, as shown in FIGS. 7 D-F. The 3D rendering showed that this small gap occurred in only a very small region and the majority of the defect was healed, as shown in FIG. 7 D. Histology showed disorganized fibrous connective tissue between the bones of the defect, as shown in FIG. 7 F. Hydrogels containing rmGremlin1 caused a dose dependent decrease in the amount of bone present in the defect, as shown in FIGS. 6 G-L. None of these animals displayed bridging of the defect and histology showed more fibrous connective tissue within the defect, as shown in FIGS. 7 I and L. Additionally, the 2D μCT images showed a lack of the thick trabecular structure that was seen in the empty or hydrogel+carrier defects, as shown in FIGS. 7 H and K. The defects containing the un-polymerized PEG-N3 also had nearly completed bridging of the defect and the thick trabecular structure that was seen with the empty defects, as shown in FIGS. 7 M-O, indicating that the highest dose of rmGremlin1 did not have any effect on defect healing in the absence of a cross-linked gel.

Quantification of Defect Healing

The extent of bone regeneration was assessed using μCT and an advanced segmentation algorithms described above. On post-op day 5 there was a decrease in the defect width, a slight decrease in the distance for the hydrogel+carrier group, but for both of the groups containing rmGremlin1 there was no decrease in the distance from the initial 1.50 mm wide defect, as shown in FIG. 8 A. By 14 days post-op there was a decrease in the width for both the hydrogel+carrier and lower dose hydrogel+300 ng group, but there was no change in the width of the higher hydrogel+500 ng group, indicating there was a dose dependent decrease in the defect width in response to the hydrogel/inhibitor composite. As seen previously, the defect was bridged early in the empty defects as no changes were seen between 5 and 14 days post-op. PEG-N3+500 ng rmGremlin1 delivered to the polymer hydrogel did not have any impact on bone healing, as there were no differences at either time point between this group and the empty defect. There were no differences among any of the groups on post-operative day 5 in the defect thickness, defect mineral content, and defect bone volume, as this time point is before the defect undergoes the mineralization that is part of the normal defect healing, as shown in FIGS. 8 B-D. For both the defect mineral content and bone volume there was a dose dependent decrease on post-op day 14; while there was no difference among the empty, hydrogel+carrier, and PEG-N3+500 ng groups, as shown in FIGS. 8 C-D. Additionally, there were no changes in any of the parameters between days 5 and 14 for the hydrogel+500 ng group indicating that there was no significant bone growth observed with these defects.

The results clearly demonstrate that the polymer hydrogel allows for rapid in situ polymerization for controlled delivery of therapeutic proteins. Polymerization of PEG-N3 and DBCO-PEG to form hydrogels resulted in very rapid cross-linking that occurs spontaneously without the need for any additional initiators. The polymerization for all applications resulted in a fully cross-linked polymer hydrogel in less than 90 seconds. This rapid spontaneous polymerization has the potential to deliver incorporated factors to any site that can be reachable with a needle. Furthermore, incorporated proteins retained their biological activity both in vitro and in vivo.

This appears to be the first time Gremlin has been delivered to delay the rapid bone growth seen in pediatric patients. Not only does this have tremendous potential to delay the post-operative re-synostosis frequently seen in cases of craniosynostosis, but it also has the potential to dramatically change the surgical management of this disease. This therapy could allow for the endoscopic removal of the fused suture and in effect re-create the function of a normal suture. This minimally invasive procedure has been abandoned as the results from the surgery were temporary. Outside of craniofacial reconstruction, delaying the rate of bone growth has direct applications in treating fractures of the growth plate and heterotopic ossification. In addition to delivering BMP inhibitors, the plug and play architecture of the PEG-N3 RAFT polymerization also allows the polymer hydrogel to be used for other regenerative applications that may necessitate cell adhesion peptides, cleavable linkages, or covalent attachment of therapeutic small molecules.

In Vitro Hydrogel Testing

All in vitro experiments were performed under aseptic conditions. Aqueous stock solutions of DBCO-PEG (12.5%, 6.25%, 4.85%, 3.13%, 1.56%; w:v) and PEG-N3 (50%; w:v) were prepared by sonicating the polymers in PBS at room temperature. Two parts DBCO-PEG and 1 part PEG-N3 were incubated on ice until mixing by pipetting and injected in to a modified syringe mold. The gels were then incubated at 37° C. in 1 mL of PBS with 10% FBS until testing. Unconstrained compression testing was performed with the samples immersed in PBS, a 0.1±0.01 N preload, a displacement of 3 mm, and a 2 mm/s compression velocity (Bose EnduraTEC 3100, Bose Corporation, Eden Prairie, Minn.). GST was fluorescently labeled with Alexa Fluor 647 carboxylic acid, succinimidyl ester using the manufacturer's protocol, purified with a PD 10 column, lyophilized overnight, and re-suspended in sterile PBS. Aliquots were diluted 1:5 in sterile PBS and quantified by fluorometry. The biological activity of rmGremlin1 (R&D Systems, Minneapolis, Minn.) delivered from the 12.5% w:v hydrogel was performed by incubating gels containing 150 ng rmGremlin1 or 4 nm HCl vehicle at 37° C. for 7 days in DMEM. Serum and 100 ng/mL rhBMP2 (R&D Systems) or vehicle was added to conditioned medium when MG63 cells were at 80% confluence. After 24 hours cells alkaline phosphatase activity was measured as previously described[20].

Defect Creation

All procedures were approved by the Georgia Tech Institutional Animal Care and Use Committee in accordance with the guide for the Care and Use of Laboratory Animals. All calvarial defects were created in post-natal day 21 old male C57Bl/6J mice. This is the age at which the mice are weaned and that the PF suture has fused with osteoid but the tissue has not yet undergone mineralization to any great extent[14]. Under 28× magnification a 1.5 mm by 2.5 mm defect was made removing the PF suture using a piezoelectric instrument under constant irrigation with sterile PBS as previously described. As appropriate the defects were left empty or injected with 2 μL of the 12.5% hydrogel with the appropriate concentration of rmGremlin1 or GST-647. The ratios and mixing were performed as described above and the polymerization was verified after 20 seconds with a blunt 25G needle. All mice were randomized to both the treatment group and post-operative time point (N=5 per group) with all analysis conducted by a blinded reviewer. Fluorescence release from mice containing either the hydrogel+GST-647 or PEG-N3+GST-647 were anesthetized and imaged on post-operative days 0, 2, 5, and 14 (IVIS Lumina II) (2 groups n=5). Total fluorescent counts over the entire head and in a 1.5 mm by 2.5 mm were determined using the same display scales.

The effect of rmGremlin1 delivered from the hydrogel was assessed by creating the cranial defects described above and randomized to contain 2 uL of: empty defect, hydrogel only, hydrogel+300 ng rmGremlin1, hydrogel+500 ng rmGremlin1, and the un-polymerized PEG-N3+500 ng rmGremlin1 (5 groups, n=10). On post-op days 5 and 14, mice were euthanized and imaged with μCT with a voxel size of 31 um (VivaCT 40, Scanco Medical, Basset, Switzerland). The extent of bone regeneration in the defect was assessed using an advanced segmentation algorithm described and validated previously[9,21]. Histological assessment was performed using haematoxylin and eosin stained 7 μm axial sections.

Demonstration of Polymerization in Defect Control Tests.

The polymer hydrogel has been tested in a mouse calvarial defect. A 1.5 mm by 2.5 mm defect was created to remove the posterior frontal suture in juvenile mice. Prior work by the inventors has shown that this defect heals within the first week following surgery. The mice from the study were randomized to either contain an empty defect or have the polymer hydrogel injected in the defect. The polymer hydrogel did not contain any bioactive molecules. There were no complications in injecting the polymer hydrogel directly onto exposed dura and there were no postoperative complications. The mice were scanned with micro-computed tomography 5 and 10 days following surgery and processed with a previously developed algorithm. The algorithm is a modification to the snake algorithm and has been validated to be within 1% of the serial histology measurements. The algorithm measured the distance between the bones, the percentage of the defect open, the area of bone in the defect, the volume of bone in the defect, and the mass of bone in the defect. There were no significant changes in any of the measurements at either time point. This suggests that the injecting the polymer hydrogel to polymerize in-situ does not negatively impair bone healing or have a significant effect on the surrounding tissues. In addition, MRI scans of the mice have showed that the polymer hydrogel remains in the defect and the polymerization does not disrupt the underlying dura.

Statistical Analysis

All data are represented as the mean±standard error of the mean. The sample size for all in vivo and in vitro experiments was determined by a prospective power analysis based on previously reported data. All cell culture experiments were performed with six independent cultures (n=6) and repeated two times. All in vivo experiments were performed in 5 mice per group per time point (n=5). The normality of the data was verified by the D'Agistino-Pearson omnibus normality test. For all in vitro experiments a one way ANOVA was performed and where appropriate significance among groups was determined by a multiple comparison test with Bonferroni adjustments. For all in vivo experiments a two way ANOVA was performed and as expected there was a significant (P<0.001) effect of treatment group, time, and interaction for all analyses. Since interactions were found significant, main effect significance was tested by either a conditional one way ANOVA with Bonferroni multiple comparison post-test or an un-paired two-sided t-test not assuming equal variance. Statistical significance for all experiments was declared when the p-value was less than 0.05.

The following publications in their entireties are hereby incorporated by reference into this application as if fully set forth herein in order to more fully describe the state of the art to which the disclosed matter pertains.

Kolb, H. C., Finn, M. G. & Sharpless, K. B. Click Chemistry: Diverse Chemical Function from a Few Good Reactions. *Angew Chem Int Ed Engl* 40, 2004-2021 (2001).

Hein, J. E. & Fokin, V. V. Copper-catalyzed azide-alkyne cycloaddition (CuAAC) and beyond: new reactivity of copper(I) acetylides. *Chem Soc Rev* 39, 1302-1315 (2010).

DeForest, C. A., Polizzotti, B. D. & Anseth, K. S. Sequential click reactions for synthesizing and patterning three-dimensional cell microenvironments. *Nat Mater* 8, 659-664 (2009).

Ning, X., Guo, J., Wolfert, M. A. & Boons, G. J. Visualizing metabolically labeled glycoconjugates of living cells by copper-free and fast huisgen cycloadditions. *Angew Chem Int Ed Engl* 47, 2253-2255 (2008).

Hermann, C. et al. Rapid Re-synostosis Following Suturectomy in Pediatric Mice is Age and Location Dependent. *Bone Submitted* (2012).

Hermann, C. D. et al. Biphasic Fusion of the Murine Posterior Frontal Suture Part 1: Complete Time Course. *Plast Reconstr Surg Submitted* (2012).

Walsh, D. W., Godson, C., Brazil, D. P. & Martin, F. Extracellular BMP-antagonist regulation in development and disease: tied up in knots. *Trends Cell Biol* 20, 244-256 (2010).

Lee, S. Y. et al. Unconfined compression properties of a porous poly(vinyl alcohol)-chitosan-based hydrogel after hydration. *Acta Biomater* 5, 1919-1925 (2009).

Khokha, M. K., Hsu, D., Brunet, L. J., Dionne, M. S. & Harland, R. M. Gremlin is the BMP antagonist required for maintenance of Shh and Fgf signals during limb patterning. *Nat Genet.* 34, 303-307 (2003).

Topol, L. Z. et al. Biosynthesis, post-translation modification, and functional characterization of Drm/Gremlin *J Biol Chem* 275, 8785-8793 (2000).

Hsu, D. R., Economides, A. N., Wang, X., Eimon, P. M. & Harland, R. M. The Xenopus dorsalizing factor Gremlin identifies a novel family of secreted proteins that antagonize BMP activities. *Mol Cell* 1, 673-683 (1998).

Bergmeyer, H. U., Bergmeyer, J. & Grassl, M. *Methods of enzymatic analysis.* 3rd edn, (Verlag Chemie, 1983).

Hermann, C. D. et al. Algorithm to Assess Cranial Suture Fusion with Varying and Discontinuous Mineral Density *Annals of Biomedical Engineering* In Press (2012).

Cooper, G. M. et al. Noggin inhibits postoperative resynostosis in craniosynostotic rabbits. *J Bone Miner Res* 22, 1046-1054 (2007).

Cooper, G. M. et al. Ex vivo Noggin gene therapy inhibits bone formation in a mouse model of postoperative resynostosis. *Plast Reconstr Surg* 123, 94S-103S (2009).

The embodiments of the present invention are not limited to the particular formulations, process steps, and materials disclosed herein as such formulations, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of this disclosure have been described in detail with particular reference to exemplary embodiments, those skilled in the art will understand that variations and modifications can be effected within the scope of the disclosure as defined in the appended claims. Accordingly, the scope of the various embodiments of the present invention should not be limited to the above-discussed embodiments, and should only be defined by the following claims and all equivalents.

The invention claimed is:

1. A composition comprising a polymer hydrogel, the polymer hydrogel comprising:
a polyacrylate backbone comprising a structure according to Formula II

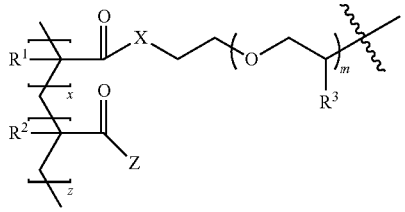

wherein
$R^1$ and $R^2$ are each independently hydrogen or a $C_1$ to $C_6$ hydrocarbon;
$R^3$ is hydrogen or methyl;
X is —O—, —S—, or —NR—;
Z is —$OR^6$, —$SR^6$, or $NR^5R^6$;
m is greater than or equal to 1;
x is an integer greater than zero and z is zero or an integer greater than zero;
$R^5$ is hydrogen or $C_1$ to $C_6$ hydrocarbon; and
$R^6$ is hydrogen, $C_1$ to $C_6$ hydrocarbon or a polyglycol chain of two to ten glycol units;
a crosslinking member comprising a structure according to the Formula III

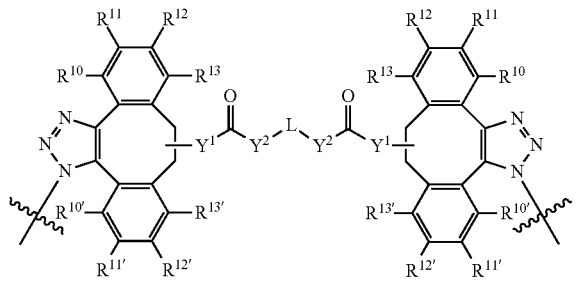

wherein
each $R^{10}$, $R^{11}$, $R^{12}$, $R^{13}$, $R^{10'}$, $R^{11'}$, $R^{12'}$, and $R^{13'}$ is independently hydrogen, $C_1$ to $C_6$ alkyl, $C_1$ to $C_6$ alkoxy, nitro, fluoro, chloro, or bromo;
$Y^1$ and $Y^2$ is each independently —O—, —S—, or —$NR^4$—;
wherein $R^4$ is hydrogen or a $C_1$ to $C_6$ hydrocarbon; and
L comprises a polyglycol;
wherein the polyacrylate backbone and the crosslinking member are spontaneously polymerized to link the polyacrylate backbone and crosslinking member at the triazole ring to form the polymer hydro gel; and
a therapeutic agent not chemically bonded to the polymer hydrogel.

2. The composition of claim 1, wherein $Y^1$ is —NH— and $Y^2$ is —O—.

3. The composition of claim 1 wherein L comprises 10-100 ethylene glycol units.

4. The composition of claim 3, wherein L further comprises one or more ester, amide, carbonate, carbamate, or urea groups, or a mixture thereof.

5. The composition of claim 1 wherein $R^{10}$, $R^{11}$, $R^{12}$, $R^{13}$, $R^{10'}$, $R^{11'}$, $R^{12'}$, and $R^{13'}$ are each independently hydrogen or fluoride.

6. The composition of claim 1, wherein when z is greater than zero, the ratio of x to z is between about 5:1 to about 2:1.

7. The composition of claim 1, wherein m is from 2 to about 6.

8. The composition of claim 1, wherein the polyacrylate backbone and the crosslinking member are connected through the triazole ring.

9. The composition of claim 1, wherein the polymer hydrogel has a structure of Formula IX:

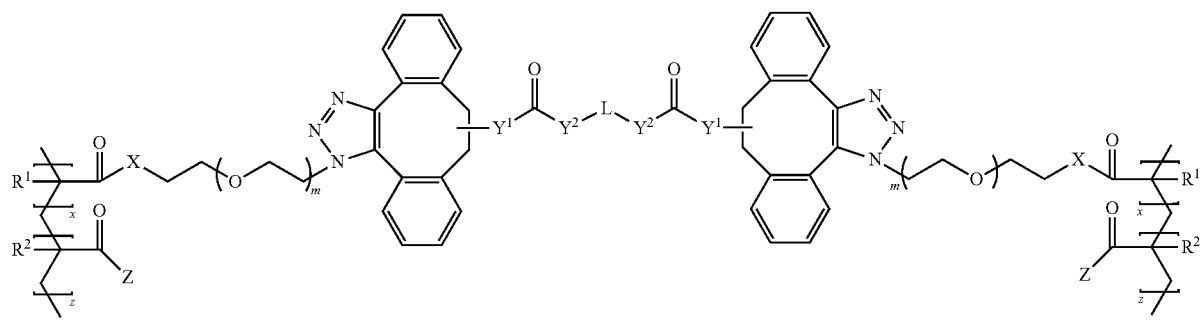

wherein
- $R^1$ and $R^2$ are each independently hydrogen or a $C_1$ to $C_6$ hydrocarbon;
- x is an integer greater than zero, z is zero or an integer greater than zero;
- X is —O— or —$NR^5$—;
- $Y^1$ is —NH— and $Y^2$ is —O—;
- Z is —$OR^6$ or $NHR^6$, wherein $R^6$ is hydrogen, $C_1$ to $C_6$ hydrocarbon or a polyethylene glycol chain of two to ten ethylene glycol units;
- m is greater than or equal to 2, and
- L comprises a polyethylene glycol.

10. The composition of claim 1, wherein the therapeutic agent is a protein of between about 15 and about 35 kDa.

11. The composition of claim 1, wherein the therapeutic agent is a recombinant protein that inhibits BMP.

12. The composition of claim 1, wherein the polymer hydrogel is at a concentration of about 1.5% to about 15% weight to volume of water.

13. The composition of claim 1, wherein said spontaneous polymerization of said polymer hydrogel is complete in less than three minutes.

14. The composition of claim 1, wherein said polymer hydrogel achieves gelation within ninety seconds.

\* \* \* \* \*